United States Patent
Foresta et al.

(12) 
(10) Patent No.: US 6,180,667 B1
(45) Date of Patent: *Jan. 30, 2001

(54) ESTERS OF ACYL L-CARNITINES AND PHARMACEUTICAL COMPOSITIONS CONTAINING SAME FOR TREATING ENDOTOXIC SHOCK

(75) Inventors: Piero Foresta, Pomezia; Vito Ruggiero; Maria Ornella Tinti, both of Rome; Nazareno Scafetta, Pavona di Albano, all of (IT)

(73) Assignee: Sigma-Tau Industrie Farmaceutiche Riunite S.p.A., Rome (IT)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/827,448

(22) Filed: Mar. 28, 1997

Related U.S. Application Data

(62) Division of application No. 08/274,686, filed on Jul. 14, 1994, now Pat. No. 5,625,085.

(30) Foreign Application Priority Data

Jul. 14, 1993 (IT) ............................. RM93A0468

(51) Int. Cl.⁷ .................................................. A61K 31/225
(52) U.S. Cl. .............................. 514/547; 554/90; 554/91; 554/94; 554/101; 554/104; 554/105; 554/110; 560/149; 560/150; 560/153; 560/170

(58) Field of Search ................................... 554/90, 91, 94, 554/101, 104, 105, 110; 560/149, 150, 153, 170; 514/547

(56) References Cited

U.S. PATENT DOCUMENTS

| | | |
|---|---|---|
| 4,439,438 | 3/1984 | Cavazza . |
| 5,041,643 | 8/1991 | Tinti et al. . |
| 5,412,113 | 5/1995 | Giannessi et al. . |
| 5,491,260 | 2/1996 | Giannessi et al. . |
| 5,498,632 | 3/1996 | Santaniello et al. . |
| 5,498,633 * | 3/1996 | Santaniello ........................... 514/547 |
| 5,519,056 | 5/1996 | Santaniello et al. . |
| 5,532,409 | 7/1996 | Giannessi et al. . |
| 5,543,556 | 8/1996 | Tinti et al. . |
| 5,625,085 * | 4/1997 | Foresta ................................ 554/107 |

FOREIGN PATENT DOCUMENTS 442850  8/1991  (EP) .

* cited by examiner

Primary Examiner—Michael L. Shippen
(74) Attorney, Agent, or Firm—Oblon, Spivak, McClelland, Maier & Neustadt, P.C.

(57) ABSTRACT

Esters of alkanoyl L-carnitines wherein the alkanoyl is a saturated or unsaturated, staight or branched alkanoyl having 2-26 carbon atoms, optionally ω-substituted with trialkylammonium, dialkylsulfonium, hydroxyl, carboxyl, halogen, methanesulfonyl and hydroxysulfonyl, are useful for preparing pharmaceutical compositions for the treatment of endotoxic shock.

8 Claims, 14 Drawing Sheets

ESTERS OF ACYL L-CARNITINES AND PHARMACEUTICAL COMPOSITIONS CONTAINING SAME FOR TREATING ENDOTOXIC SHOCK

This is a Division, of application Ser. No. 08/274,686 filed on Jul. 14, 1994, now U.S. Pat. No. 5,625,085.

The present invention relates to the use of esters of alkanoyl L-carnitines for producing pharmaceutical compositions suitable for treating endotoxic shock.

Since, as it will be described in detail hereinbelow, some of these esters are novel compounds, the present invention also relates to these novel esters.

The esters suitable for the use according to the invention have the formula (I)

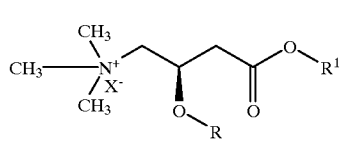

wherein:

R is a saturated or unsaturated, straight or branched alkanoyl, having 2-26 carbon atoms, optionally ω-substituted with a $R_2$ group selected from trialkylammonium or dialkylsulfonium wherein the alkyl group has 1-3 carbon atoms: hydroxyl; carboxyl; halogen; methanesulfonyl and hydroxysulfonyl;

$R_1$ is a saturated or unsaturated, straight or branched alkyl having 2-26 carbon atoms, optionally ω-substituted with $R_2$, wherein $R_2$ has the previously defined meaning, and $X^-$ is the anion of a pharmacologically acceptable acid.

Esters of alkanoyl L-carnitines are already known. U.S. Pat. No. 4,439,438 discloses compounds having the foregoing formula (I) wherein R is a straight or branched alkanoyl having 2-4 carbon atoms optionally substituted with halogen atoms or hydroxyl, or pantothenyl or linoleyl; $R_1$ is an optionally substituted straight or branched alkyl having 1-5 carbon atoms.

These compounds are used for the therapeutical treatment of myocardial hypocontractility and as antidepressants.

Esters of alkanoyl L-carnitines having the formula (I) wherein R is a straight of branched alkanoyl having 2-16 carbon atoms. $R_1$ is a straight alkyl having 11-16 carbon atoms and $X^-$ is the anion of a pharmacologically acceptable acid [typically, isovaleryl L-carnitine undecyl ester chloride (ST 722)] were disclosed in EP 0552137 A2 and EP 0552138 A2 both published after the priority date of the present application.

The pharmacological activities reported for these esters comprise the antibacterial activity (particularly against bacterial belonging to the genera Campylobacter and Helicobacter) and the antimycotic activity, particularly against yeast-like fungi (Candida albicans) and filamentous fungi (Aspergillus fumigatus), respectively.

Also EP 0559625, published after the priority date of the present application, discloses esters having the formula (I) wherein R is hydrogen or a saturated or unsaturated, straight or branched alkanoyl having 2-26 carbon atoms and $R_1$ is a saturated or unsaturated, straight or branched alkyl radical having 4-26 carbon atoms, which are endowed with myorelaxant activity selectively directed towards the gastrointestinal tract.

The pharmacological properties and therapeutical utilizations described for all the aforesaid known alkanoyl L-carnitine esters are totally remote from and unrelated to the activity (protective action against endotoxic shock) of the compounds of the present invention.

Finally, in order to complete the prior art background relevant to the present invention, reference is made to U.S. Pat. No. 4,771,075 which discloses the use of acetyl L-carnitine (i.e. an alkanoyl carnitine not an ester thereof) for treating various shock conditions, comprising septic shock. In addition to the structural dissimilarity between acetyl carnitine and the aforesaid alkanoyl carnitine esters, a marked superiority of the esters having formula (I) over acetyl carnitine for treating the endotoxic shock has been shown.

It is, therefore, apparent that the compounds having the formula (I) which are not encompassed by the aforesaid prior art references are novel compounds. More specifically, are novel those esters having the formula (I) wherein:

(a) R is a saturated or unsaturated, straight or branched alkanoyl having 2-26 carbon atoms, ω-substituted with a $R_2$ group, selected from trialkylammonium or dialkylsulfonium wherein the alkyl group has 1-3 carbon atoms, hydroxyl, carboxyl, halogen, methanesulfonyl and hydroxysulfonyl and (b) $R_1$ is a saturated or unsaturated, straight or branched alkyl having 4-26 carbon atoms, ω-substituted with a $R_2$ group or (b') $R_1$ is an alkyl group having 2-3 carbon atoms, provided that R has more than 4 carbon atoms and is not linoleyl or pantothenyl;

(c) R is a saturated or unsaturated, straight or branched alkanoyl having 2-26 carbon atoms, and $R_1$ is a saturated or unsaturated, straight or branched alkyl having 2-26 carbon atoms ω- substituted with a $R_2$ group provided that:

when $R_1$ is a straight alkyl having 2 carbon atoms, ω-substituted with a $R_2$ group R is a saturated or unsaturated, straight or branched alkanoyl having 5-17 or 19-26 carbon atoms;

(d) R is a saturated or unsaturated, straight or branched alkanoyl having 2-26 carbon atoms, ω-substituted with a $R_2$ group, and $R_1$ is a saturated or unsaturated, straight or branched alkyl having 2-26 carbon atoms provided that:

when $R_1$ is a straight or branched alkkyl having 2-4 carbon atoms and R is a saturated or unsaturated, straight or branched alkanoyl having 2-4 carbon atoms, $R_2$ as substituent of R is not halogen.

Endotoxic shock is a clinical syndrome associated with a high mortality rate and characterized by various haemodynamic, immunological and biochemical abnomarlities.

Its increasing incidence places it among the most serious nosocomial pathologies, especially in intensive care units, despite the use of a variety of antibiotics, surgical drainage, intervention with vasoactive substances and metabolic support. It is estimated that approximately 100,000 people die of endotoxic shock every year in the USA.

The main cause of this type of pathology is undoudtedly severe infection with Gram-negative bacteria, whose physio-pathological effects are ascribable to LPS, a component of the outer layer of the bacterial membrane capable of causing endotoxic shock by interacting with various components of the host's immune system, particularly macrophages.

This immunocompetent cell population, in fact, releases different endogenous mediators which prove ultimately responsible for the complex pathological picture which ensues.

The fatal outcome of endotoxic shock in man has recently been linked to the systemic release of substantial amounts of various cytokines.

There are, in fact, numerous studies which show that an abnormal modulation of cytokines such as IL-1, IL-6, TNF and IFN-γ is closely related to a severe endotoxic situation.

Other inflammation mediators (PAF, LTD, BK, substance P) would also appear to be involved in the endotoxic physio-pathology.

TNF (Tumor Necrosis Factor) is in any event the cytokine which plays a crucial role as mediator in the host's response to LPS (Tracery K J, Tumor Necrosis Factor (Cachectin) in the Biology of Endotoxic Shock Syndrome.
has been demonstated in various metabolic abnormalities characterizing the course of shock (Starnes H K, Warren R S, Jeevandam M. et al. Tumor Necrosis Factor and the acute metabolic response to tissue injury in man. *J. Clin. Invest.* 1988: 82:1321), the negative prognosis of which is often related to excessively high serum concentrations of TNF (Dames P, Reuter A, Gysen P, Demonty J, Lamy M, Franchimont P. Tumor Necrosis Factor and interleukin-1 serum levels during severe sepsis in humans. *Crit. Care Med.* 1989; 17:975–978. Debets J M H, Kampmeijer R, Van Der Linden M P M H, Buurman, W A, Vand Der Linen C J. Plasma Tumor Necrosis Factor and mortality in critically ill septic patients. *Crit Care Med.* 1989; 17:489–494).

In fact, high levels of TNF are found in the serum of animals experimentally intoxicated with LPS, and animals directly inoculated with TNF develop a toxic syndrome which is indistinguishable from endotoxinaemia (Natanson C, Eichenhols P W, Danner R L. Endotoxin and Tumor Necrosis Factor challenges in dogs simulate the cardiovascular profile of human endotoxic shock. *J. Exp, Med.* 1989; 169: 823–832. Beutler B, Milsak I W, Cerami A. Passive immunization against cachectin/Tumor Necrosis Factor protects mice from lethal effect of endotoxin. *Science* 1985: 229: 869–871).

Consequently, compounds which block or antogonize TNF may be regarded as useful therapeutical candidates in the treatment of endotoxic shock.

It was found that the esters having the formula (I) are endowed with such pharmacological properties.

Preferred are the esters having the formula (I) wherein R, $R_1$, $R_2$ and $X^-$ comply with the following conditions:

When R is a saturated, straight alkanoyl, it is preferably selected from heptanoyl, octanoyl, palmitoyl and undecanoyl;

when R is branched it is preferably selected from isobutyryl, isovaleryl, isocaproyl and 2-methylhexanoyl;

when R is unsaturated it is preferably 10-undecenoyl.
$R_2$ is preferably selected from trimethylammonium, bromine and hydroxyl.

when $R_1$ is a saturated, straight group, it is preferably selected from ethyl, n-pentyl, n-heptyl, n-decyl, n-undecyl;

when to $R_1$ is branched, it is preferably selected from isobutyl, isooctyl, hexylmethylcarbyl, ethylpentylcarbyl, ethylhexylcarbyl, decylmethylcarbyl, dipentylcarbyl and methylnonilcarbyl;

when $R_1$ is unsaturated it is preferably pentylvinylcarbyl or 10-undecenyl.

$X^-$ is preferably selected from: chloride; bromide; iodide; aspartate, particularly acid aspartate; citrate, particularly acid citrate; tartrate; phosphate, particularly acid phosphate; fumarate, particularly acid fumarate; glicerophosphate; glucosephosphate; lactate; maleate, particularly acid maleate; orotate; oxalate, particularly acid oxalate; sulphate, particularly acid sulphate; trichloroacetate; trifluoroacetate and methanesulfonate.

The esters having the formula (I) can be prepared by following two distinct synthesis routes. The first process (shown in the synthesis scheme 1) comprises the steps of:

(a) halogenating an alkanoylcarnitine with a halogenating agent such as thionyl chloride or oxalyl chloride (molar ratio 1:1 to 1:4) in an inert, anhydrous organic solvent such as acetonitrile or methylene chloride, at 0–30° C., for 1–4 hours, concentrating and utilzing the raw reaction product in the following step;

(b) dissolving the acid chloride of step (a) in an inert anhydrous, organic solvent such as acetonitrile or methylene chloride and adding the alcohol $R_1OH$ optionally diluted in the same solvent, molar ratio 1:0.5–1:2 at 0–50° C., for 2–24 hours, concentrating the resultant solution and optionally purifying the compounds by silica gel chromatography;

(c) eluting the product of step (b) dissolved in water or an organic solvent on a strongly basic ionic exchange resin, such as AMBERLITE IRA 402, or a weakly basic resin, such as AMBERLIST A 21, activated with the appropriated acid HX, and isolating the end product via lyophilization or concentration.

A further process (shown in the synthesis scheme 2) comprises the steps of:

(a') reacting carnitine or an alkanoylcarnitine inner salt with the appropriate alkyl halogenide (preferably, bromide or iodide) in an inert anhydrous organic solvent, at 3–60° C., for 8–24 hours and isolating the compound via concentration;

(b') when the starting product of step (a') is carnitine, acylating the carnitine ester obtained in step (a') with the appropriate acid chloride via known procedures;

(c') eluting an aqueous or alcoholic solution of the compound of step (a') or (b') on a ionic exchange resin such as AMBERLITE IRA 402 or AMBERLIST A 21 activated with the appropriate acid HX.

SYNTHESIS SCHEME 1

SYNTHESIS SCHEME 2

EXAMPLE 1

Preparation of palmitoyl L-carnitine 2-trimethylammonium ethyl ester dichloride (ST 1058).

Palmitoyl L-carnitine (2.5 g; 0.006 moles) was suspended in 20 mL anhydrous methylene chloride. Oxalyl chloride (0.995 mL; 0.011 moles) was added to the resulting micture cooled to 0° C.

The mixture was kept under stirring at room temperature for 4 hours and then concentrated to dryness under vacuum. The residue was washed three times with anhydrous methylene chloride and then concentrated under vacuum.

The raw product thus obtained was dissolved in 20 mL methylene chloride and to the resulting solution 2-trimethylammonium ethanol chloride (0.5 g; 0.0036 moles) was added. The solution was kept overnight at room temperature and at 40° C. for 6 hours. To the solution, cooled to room temperature, ethyl ether was added till complete precipitation of the product.

The raw product was filtered off and crystallized from isopropanol. 1.7 g of the title product were obtained. Yield 50%.

TLC silica gel

| eluant: | $CHCl_3$ | IsoprOH | $CH_3OH$ | $H_2O$ | AcOH |
|---------|----------|---------|----------|--------|------|
|         | 4.2      | 0.7     | 2.8      | 1.1    | 1.1  |

$R_F = 0.2$ $[\alpha]_D^{25} = -9.1 (c=1\% \; H_2O)$

K.F. ($H_2O$ content) 1.6%

Elementary analysis for $C_{28}H_{58}Cl_2N_2O_4$

|                          | C %   | H %   | N %  | Cl %  |
|--------------------------|-------|-------|------|-------|
| Calculated with 1.6% $H_2O$ | 59.34 | 10.49 | 4.94 | 12.51 |
| Found                    | 59.18 | 11.96 | 4.86 | 12.12 |
| HPLC                     |       |       |      |       |

Column spherisorb Cl (5 μm) 1.15 cm×0.46 cm (diameter)
Temp. 45° C.
Eluant $CH_3CN$—$KH_2PO_4$ 50 mM 65–35 pH 5.45
Flow rate 1 mL/min
Detector UV λ=205 nm
$R_t$ 14.4 min.
NMR:$D_2O$ δ5.7(1 H,m,CHOCO); 4.7–4.5(2 H,m,$N^+$ $CH_2CH_2$); 4.0–3.8)4 H,m,$N^+CH_2CH;COOCH_2$); 3.3(18 H,s,2($CH_3$)$_3N^+$); 2.9(2 H,d,$CH_2COO$); 2.4(2 H,t,$OCOCH_2$); 1.6(2 H,m,$CH_2$); 1.3(24 H,s,($CH_2$)$_{12}$); 0.9(3 H,t,$CH_3$).

EXAMPLE 2

Preparation of undecanoyl L-carnitine 2-trimethylammonium ethyl ester dichloride (ST 1059).

This compound was prepared as described in Example 1, substituting undecanoyl L-carnitine for palmitoyl L-carnitine.

The raw reaction product was purified via silica gel chromatography by eluting with $CHCl_3$—$CH_3OH$ 90:10.

1.2 g of the title compound were obtained. Yield 50%.

TLC as described in Example 1.

$R_F = 0.2$ $[\alpha]_D^{25} = -8.3 (c=0.25\% \; H_2O)$

KF ($H_2O$ content) 2.5%
Elementary analysis for $C_{23}H_{48}Cl_2N_2O_2$

|  | C % | H % | N % | Cl % |
|---|---|---|---|---|
| Calculated with 2.5% $H_2O$ | 55.24 | 9.95 | 5.60 | 14.18 |
| Found HPLC | 54.12 | 10.19 | 5.52 | 12.79 | as described in Example 1
$R_t$=17.03
NMR:$D_2O$ δ5.7(1 H,m,CHOCO); 4.6(2 H,m,$N^+CH_2CH_2$); 4.0–3.8(4 H,m,$N^+CH_2CH;OCH_2$); 3.3(18 H,ds,2)$CH_3)_3N^+$); 2.9(2 H,d,$CH_2COO$); 2.4(2 H,t,$COOCH_2$); 1.6(2 H,m,$CH_2$); 1.3(14 H,s,$(CH_2)_7$); 0.8(3 H,t,$CH_3$).

EXAMPLE 3

Preparation of heptanoyl L-carnitine 5-trimethylammonium pentyl ester dichloride (ST 1071).
Preparation of 5-trimethylammonium 1-pentanol.

5-amino-1-pentanol (10.8 mL; 0.1 moles) was diluted in 100 mL $H_2O$, 250 mL $CH_3OH$ and 120 mL 10% NaOH.

To this solution $CH_3I$ (62 mL; 1 mole) and 10% NaOH sufficient to keep the pH sharply alkaline were added.

The solution was kept under stirring at 65° C. for 4 hours, then brought to dryness under vacuum. The raw product was taken up with $H_2O$ and eluted on IR 402 resin activated in $Cl^-$ form. The eluate was concentrated to dryness, the residue taken up with acetic acid and the resulting mixture filtered in order to remove any insoluble material. Ethyl ether was added to the solution till complete precipitation. 12.5 g of a product were obtained which was used as such in the following step.

Preparation of heptanoyl L-carnitine 5-trimethylammonium-pentyl ester dichloride (ST 1071)

This compound was prepared as described in Example 1, using as starting products heptanoyl L-carnitine and 5-trimethylammonium 1-pentanol.

The raw reaction product was purified via silica gel chromatography using as eluant a $CHCl_3$—$CH_3OH$ mixture, 90-10 to 80-20 gradient.

3.6 g of the title compound were obtained. Yield 76%.
TLC as described in Example 1
$R_F$=0.25
$[\alpha]_D^{25}$=-12.9 (c=1% $H_2O$)
K.F. ($H_2O$ content) 2.4%
Elementary analysis for $C_{22}H_{46}N_2O_2Cl_2$

|  | C % | H % | N % | Cl % |
|---|---|---|---|---|
| Calculated with 2.4% $H_2O$ | 54.46 | 9.82 | 5.77 | 14.61 |
| Found HPLC | 53.74 | 9.63 | 5.56 | 15.21 |

Column: Lichrosorb $NH_2$ (5 μm) 4.0 mm×250 mm
Temp.: 25° C.
Eluant: $CH_3CN$—$KH_2PO_4$ 50 mM 65-35 pH 5.4
Flow rate: 1 mL/min.
Detector: UV λ=205 nm
$R_t$: 4.9 min.
NMR: $D_2O$ δ 5.7 (1H,m, C̲HOCO); 4.2(2H,t,$OCH_2$); 4.0-3.7(2H,m,$N^+CH_2$—CH); 3.4-3.3(2H,m,$N^+CH_2CH_2$); 3.2(9H,s,$(CH_3)_3\overline{N^+}$); 3.1(9H,s,$(CH_3)_3N^+$); 2.9($\overline{2}$H,dd, $CH_2COO$); 2.5(2H,t,$OCOCH_2$); 1.9-1.2(14H,m,7$CH_2$); 0.9 (3H,t,$CH_3$).

EXAMPLE 4

Preparation of isovaleryl L-carnitine chloride 11-hydroxyundecyl ester (ST 1095)

Isovaleryl L-carnitine inner salt (1.2 g; 0.004 moles) was dissolved in 10 mL DMF. 11-bromoundecanol (5 g; 0.02 moles) was added to the solution, which was kept under stirring at 60° C. overnight. After cooling, ethyl ether was added to the solution till complete precipitation of an oily product which was isolated by decantation, washed again with ethyl ether, isolated and dried under vacuum.

2.3 g isovaleryl L-carnitine bromide 11-hydroxyundecyl ester were obtained.

The compound was purified via silica gel chromatography eluting with $CHCl_3$—$CH_3OH$ 98-2. The fractions were collected, concentrated, dissolved in water and eluted on IRA 402 resin activated in Cl form. The aqueous solution was lyophilized and 1.8 g of the title compound were obtained. Yield 75%.

TLC as described in Example 1.
$R_F$=0.2
$[\alpha]_D^{25}$=-13.7 (c=1% $H_2O$)
K.F. ($H_2O$ content) 2.7%
Elementary analysis for $C_{23}H_{46}ClNO_5$

|  | C % | H % | N % | Cl % |
|---|---|---|---|---|
| Calculated with 2.7% $H_2O$ | 58.42 | 10.55 | 3.10 | 7.84 |
| Found HPLC | 59.14 | 10.82 | 4.16 | 8.39 |

Column: nucleosil 5 SA 4.0 mm×200 mm
Temp.: 30° C.
Eluant: $CH_3CN/KH_2PO_4$ 50 mM 65:35 pH 3.5
Flow rate: 0.75 mL/min.
Detector UV: λ=205 nm
$R_t$: 9.91 min.
NMR:$D_2O$ δ 5.7(1H,m,CHOCO); 4.1(2H,t,$COOCH_2$); 4.0-3.7(2H,m,$N^+CH_2$); 3.6(2H,t,$CH_2OH$); 3.2(9H,s,$(CH_3)_3N^+$); 3.0-2.7(2H,m,$CH_2COO$); $\overline{2.3}$(2H,d,$OCOCH_2$); 2.0 (1H,mC̲H$(CH_3)_2$); 1.6-1.5(4H,dt,$CH_2CH_2$); 1.3(14H,s, $(CH_2)_7$); 1.0(6H,d,$(CH_3)_2$)

EXAMPLE 5

Preparation of isovaleryl L-carnitine chloride 10-hydroxydecyl ester (ST 1096)

The compound was prepared as described in Example 4.
$[\alpha]_D^{25}$=-14.4 (c=1% $H_2O$)
K.F. ($H_2O$ content) 3.3%
Elementary analysis for $C_{22}H_{44}NO_5Cl$

|  | C % | H % | N % | Cl % |
|---|---|---|---|---|
| Calculated with 3.3% $H_2O$ | 58.33 | 10.16 | 3.09 | 7.83 |
| Found | 57.31 | 10.70 | 3.34 | 8.09 |

HPLC as described in Example 4.
$R_t$=9.53 min.

NMR:$D_2O$ δ 5.7(1H,m, CHOCO); 4.1(2H,t,COOCH$_2$); 4.0-3.7(2H,m,N$^+$CH$_2$); 3.6(2H,t,CH$_2$OH);3.2(9H,s,(CH$_3$)$_3$N$^+$); 3.0-2.7(2H,m,CH$_2$COO); 2.3(2H,OCOCH$_2$); 2.0(1H, m,C$\underline{H}$(CH$_3$)$_2$); 1.6-1.5(4H,dt,CH$_2$CH$_2$); 1.3(12H,s,(CH$_2$)$_6$); 1.0(6H,d,(CH$_3$)$_2$)

PHARMACOLOGIC STUDY: A MODEL OF ENDOTOXIC SHOCK INDUCED IN LABORATORY ANIMALS BY LPS INJECTION

Experimental endotoxic shock, induced in laboratory animals by LPS injection, is thought to be a convenient model in mimicking the typical physiological and immunological dysregulations occurring in clinical practice during septic shock induced by Gram negative bacteria. This experimental shock model, therefore, is useful in studying the putative efficacy of new therapeutic agents, and gives valuable information regarding their possible use in human therapy (Dunn D L. Role of endotoxin and host cytokines in septic shock. *Chest* 1991; 100:164S–168S. Flohé S. Heinrich PC, Schneider J, Wendel A, and Floheé L. Time course of IL-6 TNFα release during endotoxin-induced endotoxin tolerance in rats. *Biochem Pharmacol* 1991; 41:1607–1614. Nishijima H, Weil M H, Shubin H, Cavaniles J. Hemodynamic and metabolic studies on shock associated with gram-negative septicaemia. *Medicine* 1973; 52:287–294. Suffredini A F, Fromm R E, Parker M M, Brenner M, Kovacks J A, Wesley R A, Parillo J E. The cardiovascular response of normal humans to the administration of endotoxin *N Engl J Med* 1989; 321:280–287).

In the present study acetyl-L-carnitine chloride (referred to as ST 200) has been used as a reference compound in that its activity in endotoxic shock is very well known.

As newly-invention compounds, the following substances have been used:
isovaleryl-L-carnitine chloride undecyl ester (ST 722); palmitoyl-L-carnitine chloride 2-trimethylammoniumethyl ester chloride (ST 1058); isovaleryl-L-carnitine chloride dodecyl ester (ST 1037); octanoyl-L-carnitine chloride undecyl ester (ST 1000).

After a comparative evaluation of the protective effect of ST 200 and the newly-synthesized alcanoyl L-carnitine esters in an experimental endotoxin shock model, the results obtained show that such esters possess a therapeutic efficacy—in terms of both increased survival and prolongation of the Mean Survival Time (MST) as well as health state—which is greater than that one of the reference compound.

EXPERIMENTAL MODEL OF ENDOTOXIC SHOCK: EVALUATION OF THE EFFECT OF ST 200 ON SERUM TNF LEVELS AND LETHALITY INDUCED BY LPS IN MICE.

Male C57BL/6 inbred mice (Iffa Credo) aged 6–7 weeks have been utilized (8–16 animals per experimental group).

The compound ST 200, solubilized in sterile saline, was administered to mice intraperitoneally (i.p) in a volume of 0.1 ml per 10 gr of body weight (b.w.).

In the experiments regarding serum TNF determinations, the compound was administered at the dose of 50 mg/kg at 60 min (by i.p. route) and 10 min (by intravenous route) before and after LPS injection, respectively.

To evaluate the protective effect of the compound on the LPS-induced lethality, a first experiment was performed following the same treatment protocol as the one described above for TNF.

Figure 1:
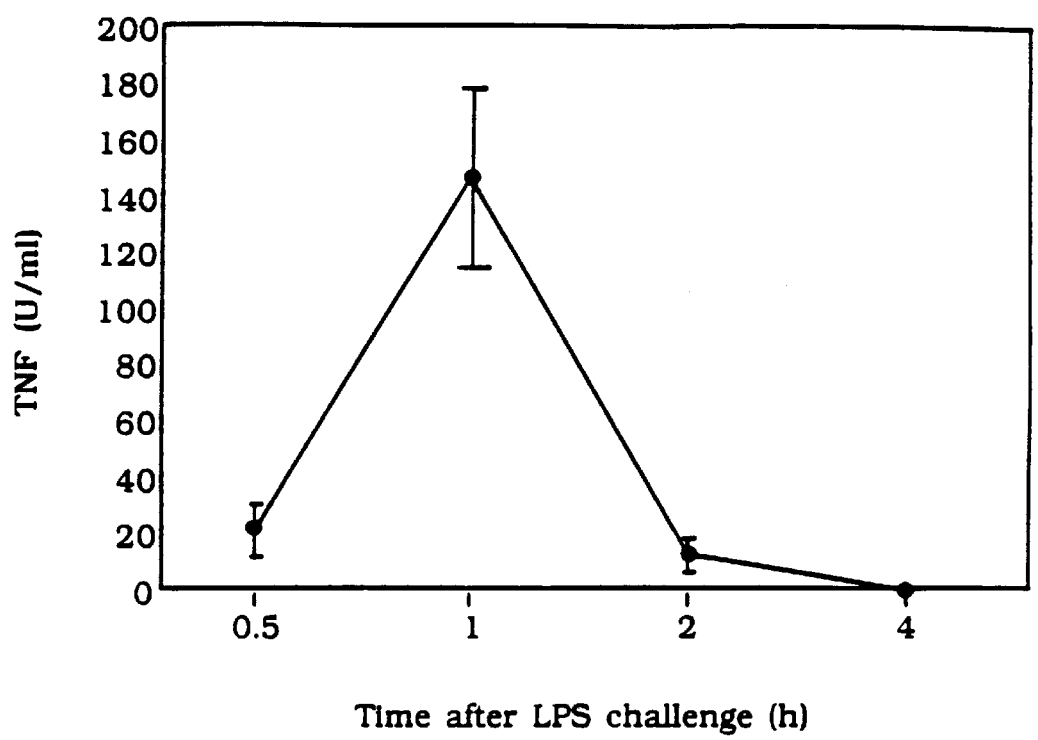
FIG. 1: Concentration of serum TNF after i.p. administration of 30 mg/kg LPS to C57BL/6 mice.

Moreover a second experiment was performed following a treatment protocol based on two daily i.p. administrations of the compound from day −1 through day +3 (once only on day 0) with respect to LPS injection (day 0). The endotoxin shock model in C57BL/6 mice was based on the i.p. administration of 30 mg/kg LPS (*E. coli* O55:B5, Difco). The LPS, when dissolved in sterile saline and injected (0.1 ml/ 10 gr b.w.) at the above-reported dose, was able to provoke the death of 60–80% of treated animals, depending on the batch. $CO_2$-anesthetized mice were bled by retro-orbital sinus puncture, and blood samples were taken 1 h following LPS injection, i.e. when TNF reached its peak levels (FIG. 1).

Blood was allowed to clot at room temperature for 2 h to separate serum, which was then centrifuged for 20 min at 4000 rpm. Samples were first aliquitted and then stored at −80° C. until assayed.

Bio-assay for TNF

Concentrations of TNF in serum were determined by using the L929 cell line (a murine fibrosarcoma), which is very sensitive to the TNF cytotoxic activity (Flick A D, and Gifford G E. Comparison of In Vitro Cell Cytotoxic Assays for Tumor Necrosis Factor. *J Immunol Met* 1984; 68:167–175). In detail, 100 μl of L929 cells (3.2×10$^5$ cells/ml) in RPMI-1640 containing 10% FCS were seeded into each well of a flat-bottomed 96-well microtiter plate (Falcon, Becton & Dickinson, Meylan Cedex, France). After incubating for 18–24 h at 37° C. in a humidified atmosphere of 5% $CO_2$, spent medium was discarded and two-fold serial dilutions (carried out in RPMI-1640 1% FCS) of serum samples (0.1 ml/well) were added in triplicate to the cells. Volumes of 0.1 ml of a 2 μg/ml solution of Actinomycin D were then added to each well. Actinomycin D inhibits RNA biosynthesis and, in so doing, amplifies the L929 sensitivity to the TNF cytotoxic activity. The mircrotiter plates were then further incubated for 18 h at 37° C. in a humidified atmosphere of 5% $CO_2$. After this incubation, the medium was discarded and the cell monolayers were washed three times with 0.9% NaCl and subsequently stained for 15 min at room temperature (RT) with 0.25% (w/v) Crystal Violet in 20% ethanol and 8% formaldehyde. After discarding the stain, the wells were gently washed in running tap water and allowed to dry at RT; the dye which had been taken up by the adering cells was eluted with 33% acetic acid and the relative absorbance at 570 nm was measured with a Multiskan MCC/340 ELISA reader (Flow Laboratories, Mclean, Va., USA). The absorbance values were then utilized to determine the TNF activity (expressed in Units/ml) of the serum samples by directly comparing the regression curve generated by the serial dilutions of each sample with the regression curve generated by the serial dilutions of a murine recombinant TNF standard having a known activity.

Evaluation of survival and health state.

For each experimental group, besides the evaluation of percent survival with respect to the total number of treated animals, the animal health state was monitored by evaluating some behavioral and physiological responses throughout the duration of the experiment (10 days ).

The statistical significance of the TNF results was evaluated by Student "t"-test. Survival data were analyzed by Fisher exact test, while changes in MST were evaluated by Mann-Whitney "U" test.

RESULTS

At the doses and schedules utilized, ST 200 is not able to significantly modulate serum TNF release (Tab. 1) nor to protect the animals from LPS-induced lethality (Tab. 2).

Moreover, the physiological responses of the animals observed throughout each experiment (10 days), namely some pathophysiological effects consequent to endotoxic shock such as reduced motility, iporeactivity to stimuli, anorexia, piloerection, body temperature, ocular exudate and so forth, did not show significant differences between treated and control groups.

FIG. 1', Concentration of serum TNF after i.p. administration of 30 mg/kg LPS to C57BL/6 mice. Values are mean (4 animals/group) ±S.D..

TABLE 1

Effect of the substance ST 200 on serum TNF levels induced by LPS (30 mg/kg, i.p.). ST 200 was administered at the dose of 50 mg/kg 60 min (by i.p. route) and 10 min (by i.v. route) before and after LPS challenge, respectively.

| Substance | Dose (mg/kg) | No. of mice | TNF U/ml (mean ± S.E.) | Variation[a] (%) | P[b] |
|---|---|---|---|---|---|
| Exp. 1 | | | | | |
| LPS | 30 | 7 | 167.5 ± 37.3 | | |
| ST 200 | 50 | 8 | 123.8 ± 25.4 | −26 | n.s. |
| Exp. 2 | | | | | |
| LPS | 30 | 8 | 276.5 ± 76.8 | | |
| ST 200 | 50 | 8 | 131.7 ± 19.5 | −52 | n.s. |

[a]= Percent mean variation of TNF levels in the treated with respect to the control group.
[b]= Student "t"-test.

TABLE 2

Protective effect of the substance ST 200 in a murine model of endotoxic shock. Evaluation of survival and mean survival time (MST).

| Substance | Dose (mg/kg) | Survival S/T[a] (%) | P[b] | MST[c] (days) | P[d] |
|---|---|---|---|---|---|
| Exp. 1 | | | | — | |
| Control | — | 10/10 (100) | | — | |
| LPS | 30 | 6/16 (37.5) | | 2.5 (2–7.5) | |
| ST 200 | 50[(1)] | 7/16 (43.75) | n.s. | 3 (2.5–10) | n.s. |
| Exp. 2 | | | | | |
| Control | — | 10/10 (100) | | — | |
| LPS | 30 | 2/10 (20) | | 2 (2–7) | |
| ST 200 | 50[(2)] | 3/10 (30) | n.s. | 2.5 (1–10) | n.s. |

Treatment was performed by i.p. injecting 30 mg/kg LPS (0 time) and administering ST 200, at the dose indicated, following protocol (1), i.e. at −60 min (i.p.) and +10 min (i.v.), or protocol (2), i.e. from day −1 through day +3 two daily i.p. injections (once on day 0).
[a]= Survivors/Total.
[b]= Fisher exact test.
[c]= Mean Survival Time with ranges of variation in brackets.
[d]= Mann-Whitney "U" test.

EXPERIMENTAL MODEL OF ENDOTOXIC SHOCK: EVALUATION OF THE EFFECTS OF ST 722 ON SERUM TNF LEVELS AND LETHALITY INDUCED BY LPS IN MICE

Male C57BL/6 inbred mice (Iffa Credo) aged 6–8 weeks have been utilized (8 animals per experimental group). The compound ST 722, solubilized in sterile saline, was given to mice intraperitoneally (i.p.) in a volume of 0.1 ml per 10 gr of body weight (b.w.).

The experiments were carried out by using ST 722 at the doses of 1.25, 2.5, 5 and 10 mg/kg, and endotoxin from *E. coli* (LPS O55:B5, Difco) at the dose of 30 mg/kg.

In the experiments regarding serum TNF determinations, the treatment with ST 722 (2.5–5–10 mg/kg) was performed by i.p. route 60 min before the i.p. injection of 30 mg/kg LPS (Protocol A), except a case where ST 722 (1.25–5 mg/kg) was administered simultaneously with LPS (Protocol B).

As for those experiments performed to evaluate the survival of the animals during endotoxic shock, the treatment with ST 722 (1.25–2.5–5 mg/kg i.p.) was performed first by i.p. route at 60 min before the i.p. injection of 30 mg/kg LPS (day 0) and then, once a day, on days +1 and +2 (Protocol #1), +1, +2 and +3 (Protocol #2), +1, +2, +3, and +4 (Protocol #3).

Experimental procedure, TNF assay, Experimental observations and Statistical analysis See the relevant paragraphs in the previous report.

RESULTS

Effect of ST 722 on serum TNF release induced by LPS

Treatment with 10 mg/kg ST 722 was able to significantly inhibit TNF secretion in two consecutive experiments ($p<0.001$ and $p<0.01$, respectively), decreasing approximately 80% of TNF release induced by LPS (Exp. 1 and Exp. 2 in Table 3).

A successive experiment showed that a serum TNF reduction to the same extend as above was also achieved when lower ST 722 doses were utilized. Actually, a significant ($p<0.001$) decrease of circulating TNF was observed at the doses of 2.5 and 5 mg/kg ST 722, corresponding to 80 and 85%, respectively, of LPS control (Exp. 3 in Table 3).

A final experiment showed that a significant ($p<0.001$) reduction of TNF release was also obtained when ST 722 was administered concurrently with LPS, although only at the dose of 5 mg/kg and not at the dose of 1.25 mg/kg (Exp. 4 Table 3).

In conclusion, these results are undoubtedly better than those obtained with the substance ST 200, which besides was administered at markedly higher doses.

Effect of ST 722 on LPS-induced lethality

Figure 2:
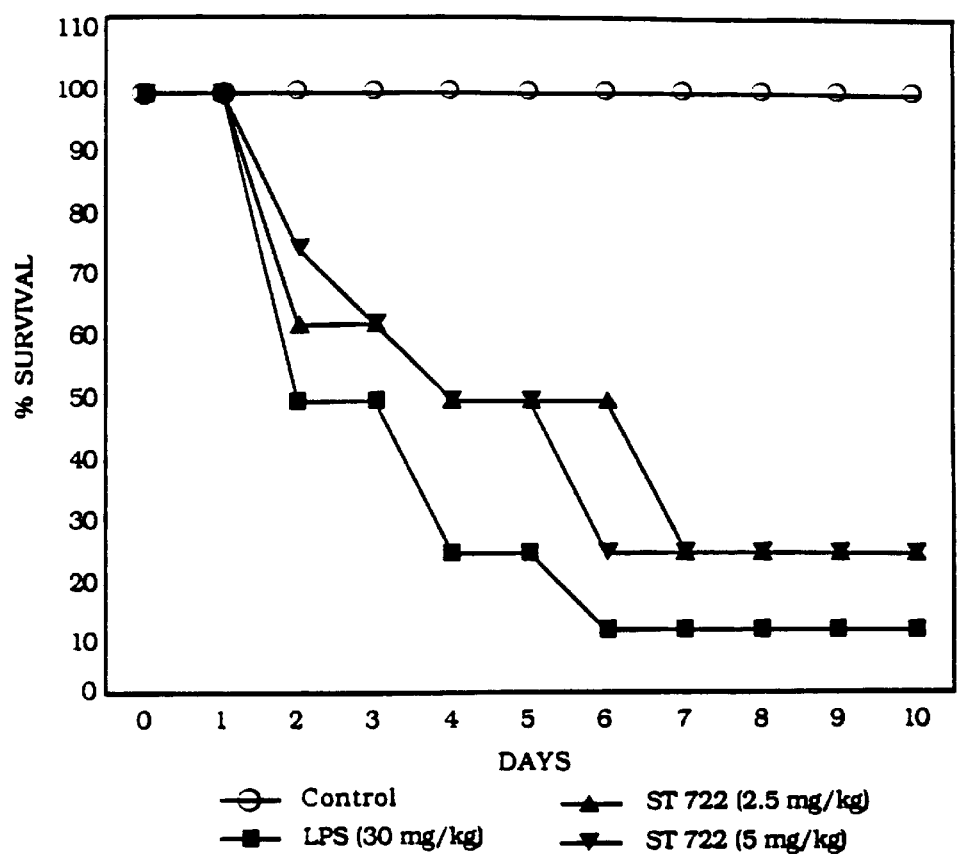
FIGS. 2–4: Effect of ST 722 treatment of lethality induced by the i.p. injection of 30 mg/kg LPS (day 0).

The overall results obtained with 3 different treatment protocols are reported in Table 4. In particular, the results of the first experiment aimed at examining the effects of repeated ST 722 treatments on LPS-induced lethality are shown in detail in FIG. 2. In this case, ST 722 treatments with 2.5 and 5 mg/kg were performed first on day 0, 60 min before the challenge with 30 mg/kg LPS, and then on days +1 and +2.

Figure 3:
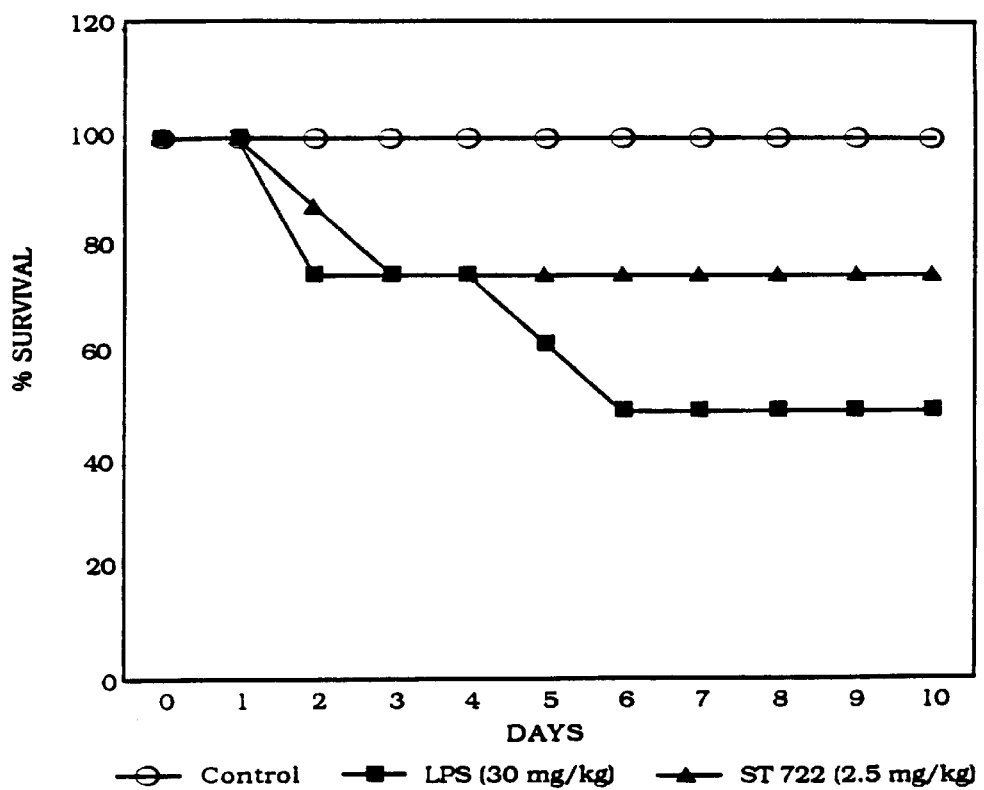

It can be noticed that ST 722, when administered following the above schedule, does not protect from LPS-induced lethality. However, if ST 722 treatment, at the dose of 2.5 mg/kg, is prolonged to day +3, an increase in the survival of treated animals is observed, although not statistically significant (FIG. 3).

Figure 4:
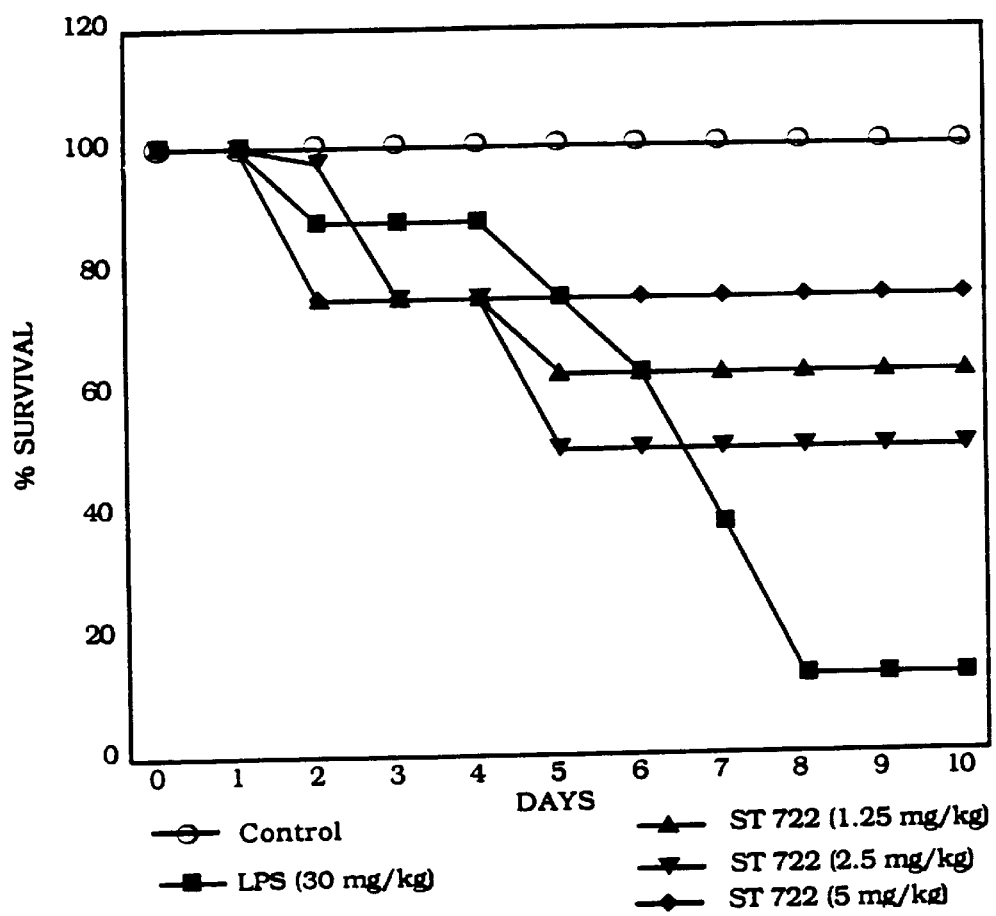

In the last experiment (FIG. 4), carried out following a protocol based on a single daily ST 722 administration from day 0 (60 min before LPS challenge) through day +4, the survival of the animals treated with 5 mg/kg ST 722 was significantly increased ($p<0.02$). Some protection, though not statistically significant, was also observed at the lower ST 722 doses, i.e. 1.25 and 2.5 mg/kg. It is worthy of note that these repeated treatments have beneficial effects on the health state of the animals. In fact, the daily food consumption per day of survival in the group of animals injected with LPS and then treated with ST 722 is higher compared to the one of animals injected with LPS and then treated with saline (Table 5).

To summarize, the percent survival as well as the health state of the animals treated with ST 722 are significantly improved with respect to the animals treated with ST 200.

TABLE 3

Effect of ST 722 treatment, at different doses, on serum TNF levels induced by LPS (30 mg/kg, i.p.). ST 722 was administered, at the reported doses, 60 min before (Protocol A) or simultaneously with the LPS challenge (Protocol B).

| Sub-stance | Dose (mg/kg) | Prot. | No. of mice | TNF U/ml (mean ± S.E.) | Variation[a] (%) | P[b] |
|---|---|---|---|---|---|---|
| Exp. 1 | | | | | | |
| LPS | 30 | A | 8 | 254.04 ± 18.16 | | |
| ST 722 | 10 | | 8 | 49.45 ± 22.86 | −81 | <0.001 |
| Exp. 2 | | | | | | |
| LPS | 30 | A | 8 | 163.52 ± 37.86 | | |
| ST 722 | 10 | | 8 | 40.92 ± 14.00 | −75 | <0.01 |
| Exp. 3 | | | | | | |
| LPS | 30 | A | 8 | 382.15 ± 63.27 | | |
| ST 722 | 2.5 | | 8 | 82.71 ± 31.89 | −79 | <0.101 |
| ST 722 | 5 | | 8 | 58.76 ± 20.25 | −85 | <0.001 |
| Exp. 4 | | | | | | |
| LPS | 30 | B | 8 | 163.61 ± 36.11 | | |
| ST 722 | 1.25 | | 8 | 128.7 ± 24.64 | −22 | N.S. |
| ST 722 | 5 | | 8 | 50.5 ± 6.13 | −70 | <0.01 |

[a]= Mean percent variation of serum TNF in the ST 722 treated group compared to LPS group.
[b]= Student "t" test.

TABLE 4

Protective effect of the substance ST 722 in a murine model of endotoxic shock. Evaluation of survival and MST.

| Substance | Dose (mg/kg) | Survival S/T (%)[d] | P[e] | MST[f] (days) | P[g] |
|---|---|---|---|---|---|
| Control | — | 8/8 (100) | | | |
| LPS | 30 | 1/8 (12.5) | | 3 (2–4.75) | |
| ST 722 | 2.5[a] | 2/8 (25) | n.s. | 5.5 (2–9.25) | n.s. |
| ST 722 | 5[a] | 2/8 (25) | n.s. | 5 (2–9) | n.s. |
| Control | — | 8/8 (100) | | | |
| LPS | 30 | 4/8 (50) | | 7.5 (2.5–10) | |
| ST 722 | 2.5[b] | 6/8 (75) | n.s. | 10 (4.25–10) | n.s. |
| Control | — | 8/8 (100) | | | |
| LPS | 30 | 1/8 (12.5) | | 7 (4.5–8) | |
| ST 722 | 1.25[c] | 5/8 (62.5) | 0.059 | 10 (2.75–10) | n.s. |
| ST 722 | 2.5[c] | 4/8 (50) | n.s. | 7.5 (3.25–10) | n.s. |
| ST 722 | 5[c] | 6/8 (75) | <0.02 | 10 (4–10) | n.s. |

[a]= ST 722 was administered by i.p. route, at the reported doses, at 60 min before LPS challenge (day 0) and then on days +1 and +2.
[b]= ST 722 was administered by i.p. route, at the reported doses, at 60 min before LPS challenge (day 0) and then on days +1, +2 and +3.
[c]= ST 722 was administered by i.p. route, at the reported doses, at 60 min before LPS challenge (day 0) and then on days +1, +2, +3 and +4.
[d]= Survivors/Total.
[e]= Fisher exact test.
[f]= Mean Survival Time with range of variation in brackets.
[g]= Mann-Whitney "U" test.

Effect of ST 722 treatment on lethality induced by the i.p. injection of 30 mg/kg LPS (day 0). ST 722 treatment, at the reported doses, was performed by administering to mice (8 animals/group) a first dose on day 0 (60 min prior to LPS challenge) and then single daily doses on days +1 and +2. Control and LPS injected animals were treated with sterile saline instead of ST 722.

Effect of ST 722 treatment on lethality induced by the i.p. injection of 30 mg/kg LPS (day 0). ST 722 treatment, at the reported doses, was performed by administering to mice (8 animals/group) a first dose on day 0 (60 min prior to LPS challenge) and then single daily doses on days +1, +2 and +3. Control and LPS injected animals were treated with sterile saline instead of ST 722.

Effect of ST 722 treatment on lethality induced by the i.p. injection of 30 mg/kg LPS (day 9). ST 722 treatment, at the reported doses, was performed by administering to mice (8 animals/group) a first dose on day 0 (60 min prior to LPS challenge) and then single daily doses on days +1, +2, +3 and +4. Control and LPS injected animals were treated with sterile saline instead of ST. 722.

TABLE 5

Evaluation of the health state (as judged by the food intake during an 11-day follow-up) of animals injected with LPS and treated with ST 722. Experimental conditions are the same as FIG. 3.

| TREATMENT | FOOD CONSUMED[a] (g) | CUMULATIVE SURVIVAL[b] (DAYS) | FOOD CONSUMED/ CUM. SURVIVAL[c] |
|---|---|---|---|
| Control | 256.10 | 88 | 2.91 |
| LPS 30 mg/kg | 41.22 | 55 | 0.75 |
| ST 722 1.25 mg/kg | 121.87 | 64 | 1.90 |
| ST 722 2.5 mg/kg | 68.49 | 59 | 1.16 |
| ST 722 5 mg/kg | 117.11 | 70 | 1.67 |

[a]= Total amount of food (g) consumed over the observation period.
[b]= Sum of the days of survival of each animal within a group, evaluated at the end of the observation period.
[c]= Mean daily food consumption of each single animal within a group during the follow-up period.

EXPERIMENTAL MODEL OF ENDOTOXIC SHOCK: EVALUATION OF THE PROTECTIVE EFFECT OF THE COMPOUNDS ST 722 AND ST 1058 ON LPS-INDUCED LETHALITY IN MICE

Male C57BL/6 inbred mice (Iffa Credo) aged 7 weeks have been utilized (7–8 animals per experimental group).

The compounds ST 722 and ST 1058, solubilized in sterile saline, were administered to mice at the dose of 1.25 mg/kg, by i.p. route, in a volume of 0.1 ml per 10 gr of body weight (b.w.).

The first two treatments were performed 1 h before and 4 h after the LPS i.p. injection (on day 0)), and went on, twice a day, through day +3 (8 administrations in total).

Experimental procedure and Statistical analysis

See the relevant paragraphs in the previous reports, except the dose of LPS, which was utilized at the dose of 35 mg/kg by i.p. route.

Figure 5:
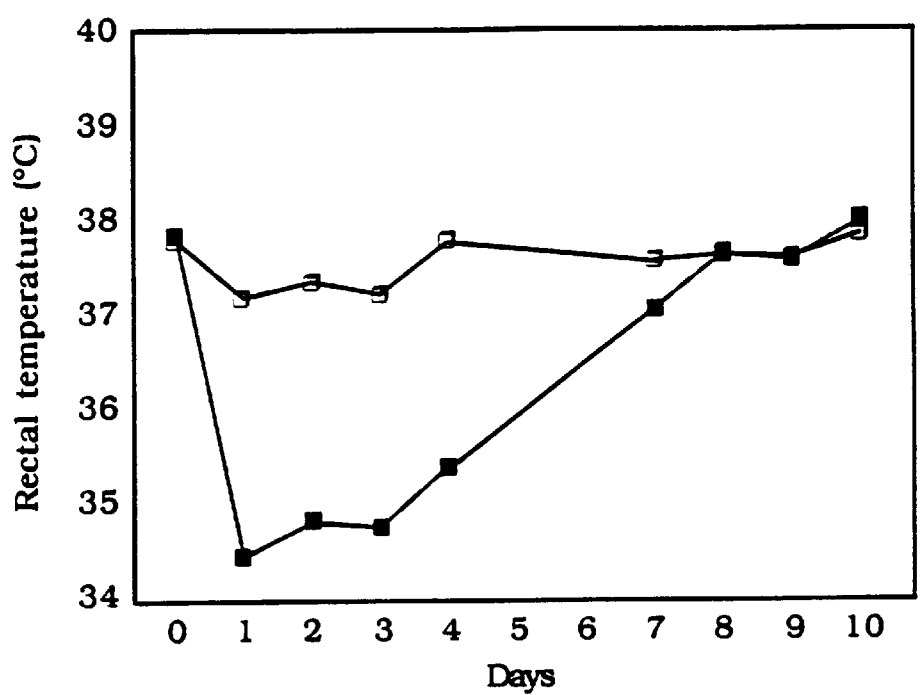

The animals (classified according to convenient identification marks) were regularly checked one by one for the duration of the experiment (10 days), and overall survival as well as health conditions were monitored. In addition to the percent survival, the Mean Survival Time (MST) was calculated at the end of the experiment. The evaluation of the health state of the animals was quantitatively assessed by determining the amount of food consumed and by measuring the rectal temperature. The former parameter was evaluated by calculating the mean food consumption both by the animals within each experimental group and by each animal per day of survival. The latter parameter was evaluated by using an arbitrary evaluation scale (score scale), which allowed to express the results as mean percent temperature variation of each group of substance- and LPS-treated animals with respect to saline-treated animals (Control group). To correctly understand the correlation between health state and registered temperature, one has to bear in mind that in this experimental model a marked hypothermia in LPS-injected animals was observed (FIG. 5). At the end of this study (see Appendix #1), strong experimental evidence is given indicating that the animal rectal temperature is a very reliable and objective criterion to evaluate the health state of the animals.

RESULTS

Figure 6:
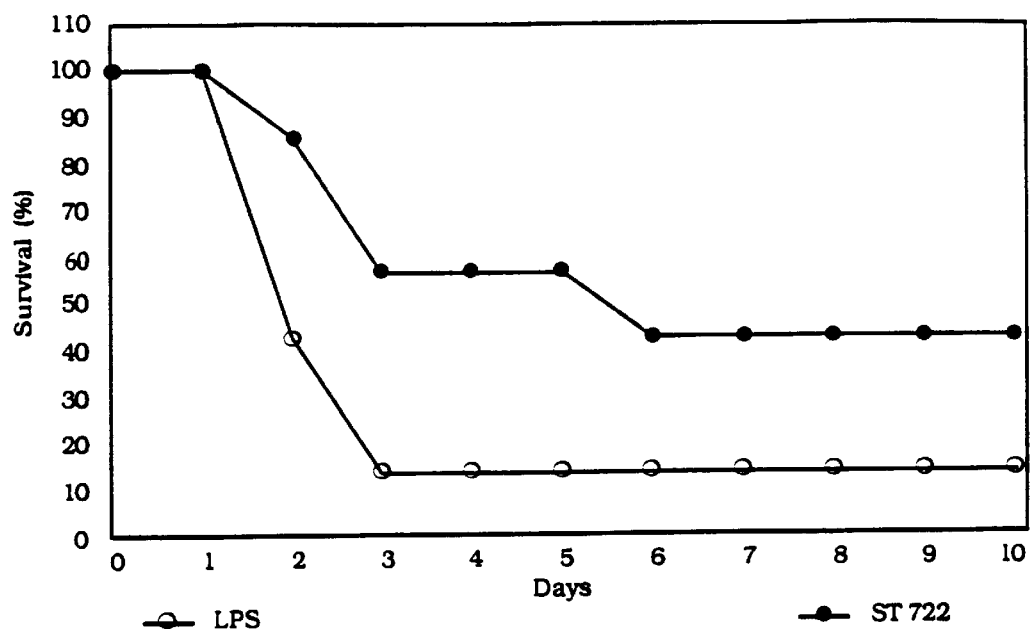
Figure 7:
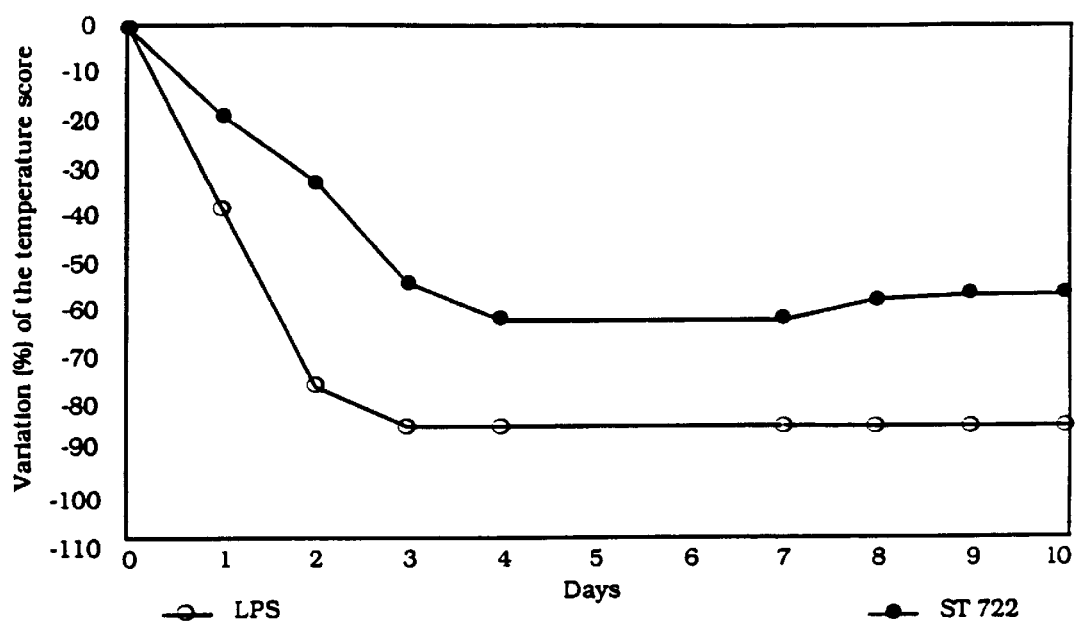

The substance ST 722 turned out to exert a protective effect, although not statistically significant, on the animals challenged with LPS: 43% of survival vs. 15% and MST of 6 vs. 2 days (Tab. 6, FIG. 6). The health state of the treated animals resulted to be better, as far the rectal temperature is concerned, than LPS-injected animals (FIG. 7).

Figure 8:
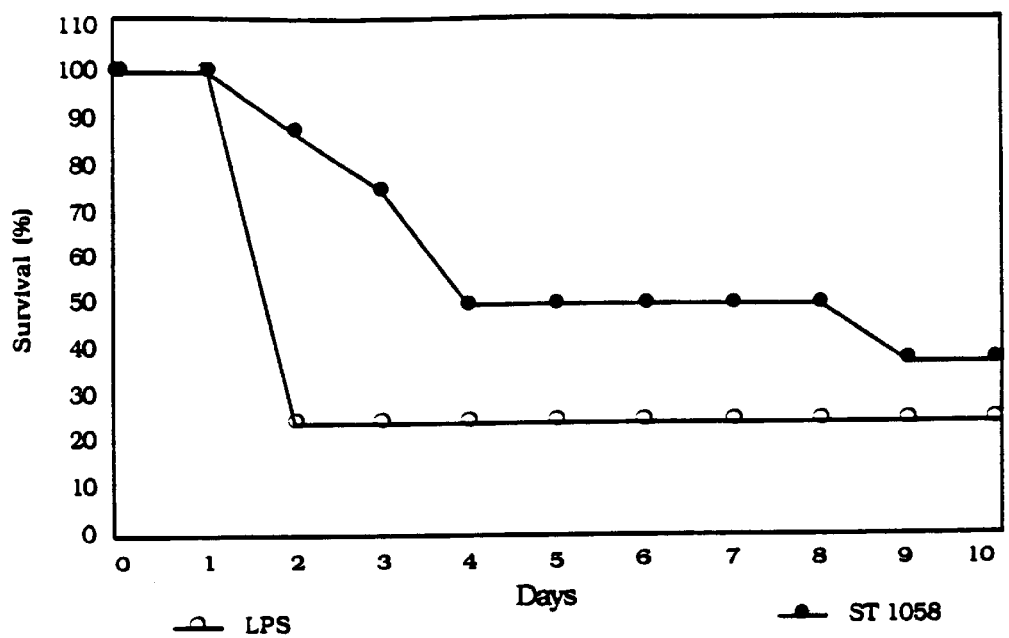
Figure 9:
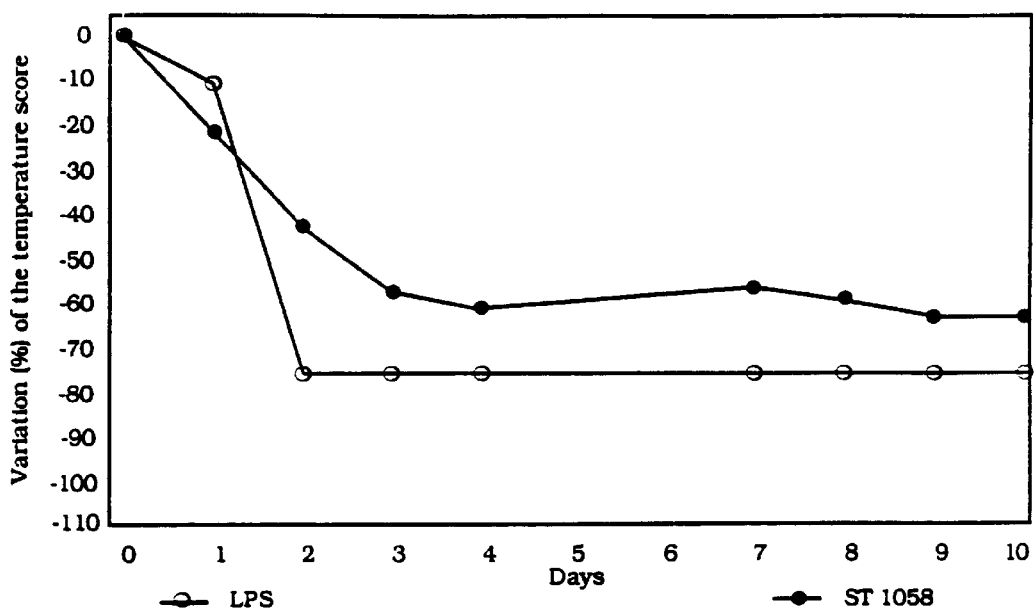

Administration of ST 1058 causes a modest increase of survival (37.5% vs. 25%) but a consistent prolongation of the mean survival time (6.5 vs. 2.0 days) (Tab. 7, FIG. 8) paralleled by ameliorated physiological conditions (increased temperature) (FIG. 9). On the whole, the results obtained with ST 722 and ST 1058 in these experiments appear to be better than those obtained with ST 200.

FIG. 5; Variation of rectal temperature of control (□—□) and LPS injected (■—■) animals. Endotoxin was given i.p. at the dose of 30 mg/kg (0 time).

TABLE 6

Protective effect of the compound ST 722 in a murine model of endotoxic shock. Evaluation of survival and MST.

| Treatment | Dose (mg/kg) | Survival S/T (%)[a] | P[b] | MST[c] (days) | P[d] |
|---|---|---|---|---|---|
| Control | — | 6/6 (100) | | — | |
| LPS | 35 | 1/7 (14.3) | | 2 (2–3) | |
| ST 722 | 1.25 | 3/7 (42.9) | n.s. | 6 (3–>10) | 0.056 |

The substance was administered, at the reported dose, by i.p. route 1 h before and 4 h after LPS challenge (on day 0) and twice daily from day + 1 through day +3.
[a]= Survivors/Total
[b]= Fisher exact test.
[c]= Mean Survival Time with range of variation in brackets.
[d]= Mann-Whitney "U" test.

FIG. 6; Survival curves in animals infected with PPS and treated with ST 722 (see Table 6 for details).

FIG. 7; Health state of the animals (See Table 6 for details).

| | b) Food intake | | |
|---|---|---|---|
| Treatment | Food intake* | Mean Survival Time (days) | Food intake per animal per day of survival** (gr/day) |
| Control | 28.98 | 10 | 2.89 |
| LPS | 4.76 | 2.57 | 1.85 |
| ST 722 | 11.21 | 5.71 | 1.96 |

*= Mean food consumption (grams) of the animals in 10 days after LPS injection.
**= Mean food consumption (grams) of one animal per day of survival.

TABLE 7

Protective effect of the compound ST 1058 in a murine model of endotoxic shock. Evaluation of survival and MST.

| Treatment | Dose (mg/kg) | Survival S/T (%)[a] | P[b] | MST[c] (days) | P[d] |
|---|---|---|---|---|---|
| Control | — | 6/6 (100) | | | |
| LPS | 35 | 2/8 (25) | | 2 (2–>8) | |
| ST 1058 | 1.25 | 3/8 (37.5) | n.s. | 6.5 (3.25–>10) | 0.052 |

The substance was administered, at the reported dose, by i.p. route 1 h before and 4 h after LPS challenge (on day 0) and twice daily from day +1 through day +3.
[a]= Survivors/Total.
[b]= Fisher exact test.
[c]= Mean Survival Time with range of variation in brackets.
[d]= Mann-Whitney "U" test.

FIG. 8; Survival curves in animals infected with LPS and treated with ST 1058 (see Table 7 for details).

FIG. 9; Health state of animals (See Table 7 for details).

| | b) Food intake | | |
|---|---|---|---|
| Treatment | Food intake* | Mean Survival Time (days) | Food intake per animal per day of survival** (gr/day) |
| Control | 31.77 | 10 | 3.17 |
| LPS | 9.39 | 3.25 | 2.89 |
| ST 1058 | 8.45 | 5.88 | 1.44 |

*= Mean food consumption (grams) of the animals in 10 days after LPS injection.
**= Mean food consumption (grams) of one animal per day of survival.

VALIDATION OF AN OBJECTIVE EVALUATION METHOD TO MONITOR THE HEALTH STATE OF ANIMALS INJECTED WITH LPS.

This study was undertaken to investigate whether there was any possibility to correlate the alteration of several behavioral parameters in LPS-injected mice with their rectal temperature. This aimed at switching from the series of experimental observations, stemming from several symptoms more or less severe provoked by the endotoxic shock and often susceptible of subjective interpretations, to a single, reliable, and objective experimental measurement: the rectal temperature. This would allow to objectively evaluate the effect exerted by a substance on the health state of animals undergoing endotoxic shock, and to avoid making a number of experimental observations in trying to adequately describe the severity of symptoms.

To this end, 90 male inbred C57BL/6 mice aged 6 weeks, utilized in 4 different experiments of LPS-induced shock, were closely followed up to 10 days after the endotoxin injection.

Six different degrees of disease were defined, and each animal was ranked according to an arbitrary evaluation scale that took into account the severity of a series of behavioral parameters, such as reduction of spontaneous activity, hyporeactivity to stimuli, anorexia, piloerection, circling, ptosis, ocular exudate etc. . . . Animal rectal temperature measurements were taken with an electronic thermometer (Termist TMS) with the appropriate thermistor.

Figure 10:
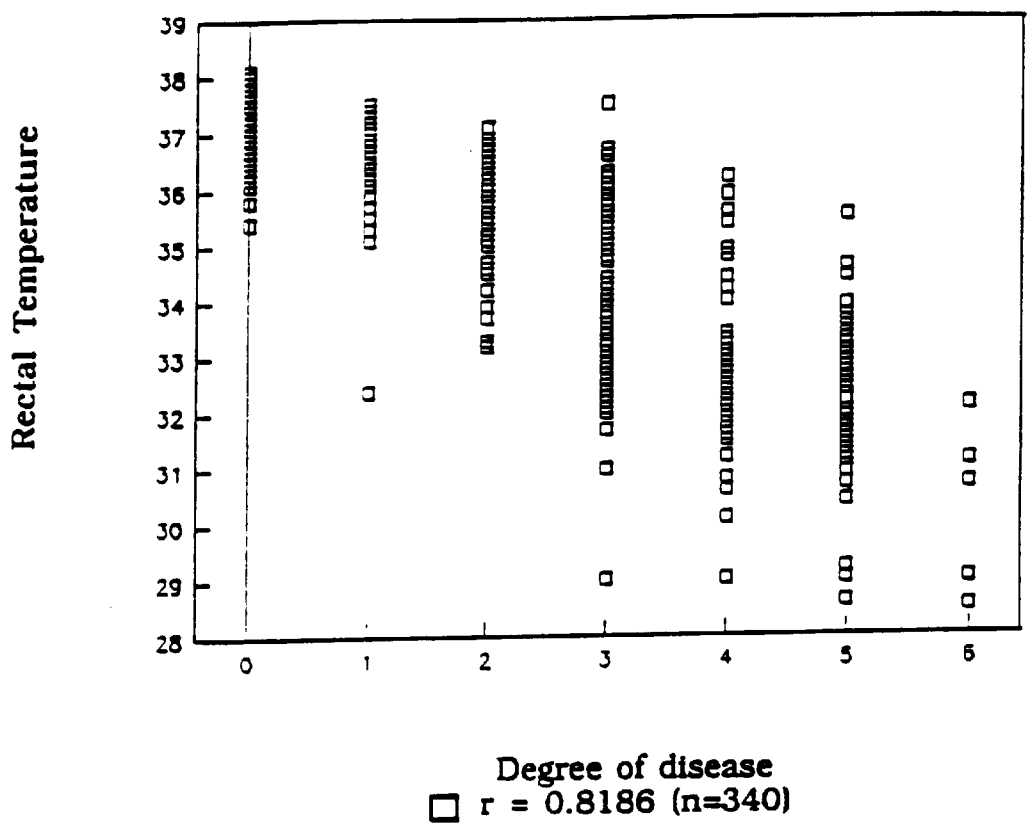

From FIG. 10, in which the correlation between degree of disease of each animal and its temperature is shown, it can be easily noticed the existence of a correlation having a very high statistical significance.

Therefore, we believe that temperature measurement in this murine model of endotoxic shock can be viewed as a useful parameter which is per se sufficient to evaluate the health state of animals (mice) undergoing endotoxic shock.

FIG. 10; Correlation between temperature and disease.

EXPERIMENTAL MODEL OF ENDOTOXIC SHOCK: EVALUATION OF THE PROTECTIVE EFFECT OF ST 722 ON LPS-INDUCED LETHALITY IN MICE

Male C57BL/6 inbred mice aged 9 weeks have been utilized (8–10 animals per experimental group). The compound ST 722, solubilized in sterile saline, was administered according to 2 different treatment schedules with respect to the LPS injection (35 mg/kg, 0 time), as follows:

a) first at −60 min (at the dose of 2.5 mg/kg i.p.) and then at +10 min (at the dose of 1.25 mg/kg i.v.)

b) from day −7 through day 0 (one hour before the LPS -challenge), at the dose of 1.25 mg/kg/day by i.p. route.

Experimental procedure and Statistical analysis

See the relevant paragraphs in the previous report.

RESULTS

Figure 11:
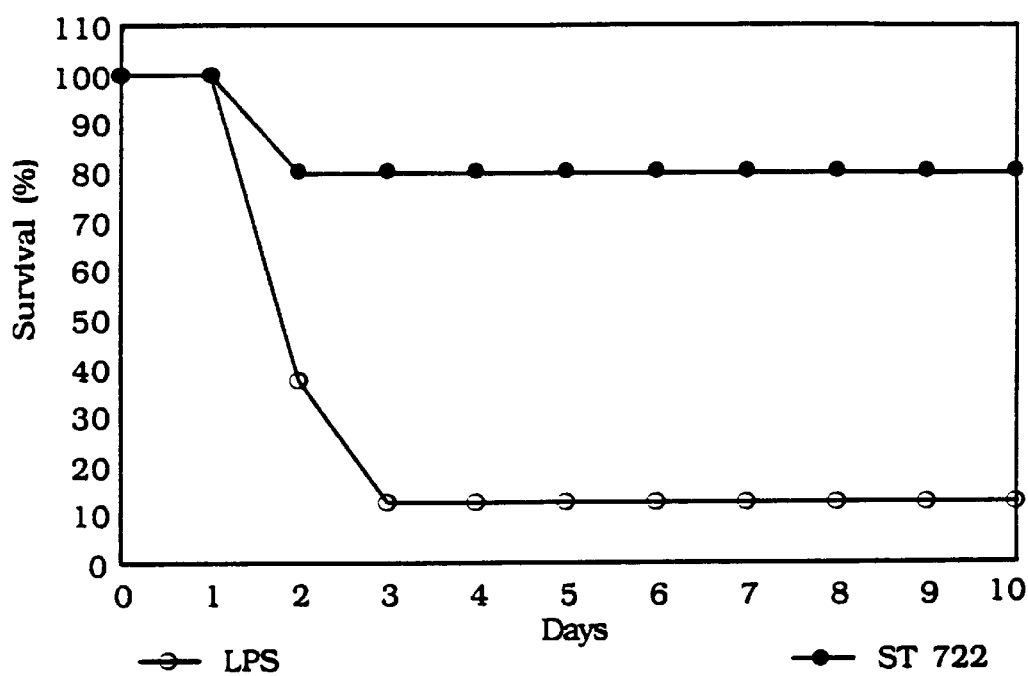
Figure 12:
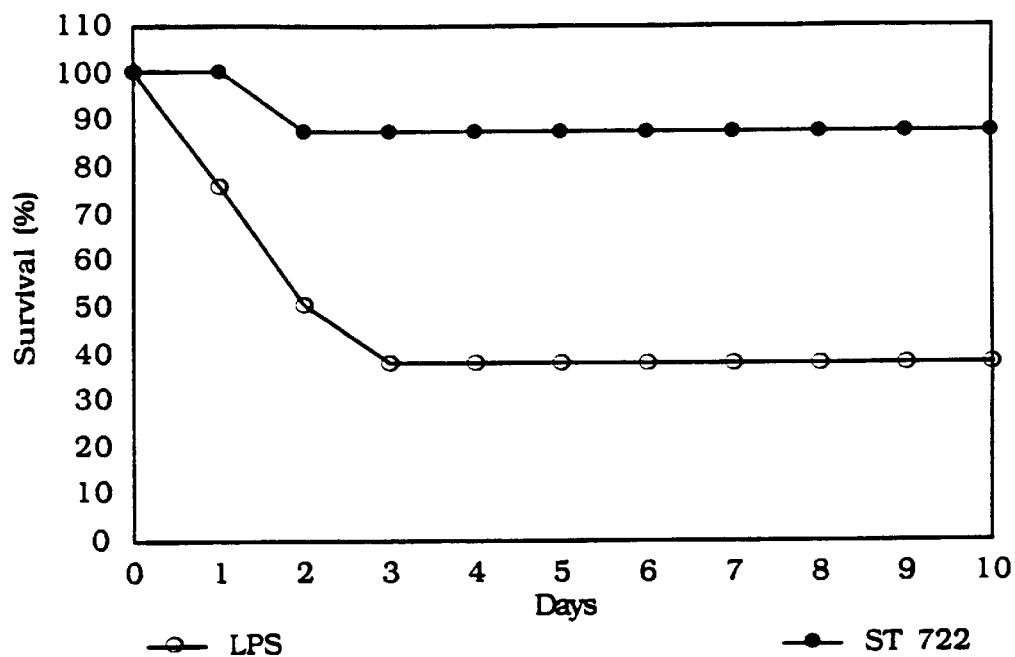

Both of treatment protocols show a marked protection of the animals intoxicated with LPS (35 mg/kg) in terms of both percent survival and MST (Table 8, FIG. 11 and FIG. 12). These results are unquestionably more favorable than those obtained with ST 200, even when the latter was used at a higher dose (50 mg/kg).

TABLE 8

Protective effect of the compound ST 722 in a murine model of endotoxic shock. Evaluation of survival and MST.

| Substance | Dose (mg/kg) | Survival S/T (%)[a] | P[b] | MST (days) | P[d] |
|---|---|---|---|---|---|
| Exp. 1 | | | | | |
| Control | — | 8/8 (100) | | | |
| LPS | 35 | 1/8 (12.5) | | 2.0 (2.0–3.0) | |
| ST 722 | 2.5 i.p. and 1.25 i.v.[(1)] | 8/10 (80) | <0.01 | ≧10 (≧8.0–≧10) | <0.02 |
| Exp. 2 | | | | | |
| Control | — | 8/8 (100) | | | |
| LPS | 35 | 3/8 (37.5) | | 2.5 (1.25–≧10) | |
| ST 722 | 1.25 i.p.[(2)] | 7/8 (87.5) | n.s. | ≧10 (≧10–≧10) | n.s. |

Treatment was performed by i.p. injecting 35 mg/kg LPS (0 time) and administering the compound ST 722 as follows:
[(1)]First at −60 min (at the dose of 2.5 mg/kg i.p.) and then at +10 min (at the dose of 1.25 mg/kg i.v.):
[(2)]From day −7 to day 0 (an hour before the LPS challenge).
[a]= Survivors/Total.
[b]= Fisher exact test.
[c]= Mean Survival Time with range of variation in brackets.
[d]= Mann-Whitney "U" test.

FIG. 11; Survival curves of animals injected with LPS and treated with the compound ST 722 (2.5 mg/kg i.p. at −60 min and 1.25 mg/kg i.v. at +10 min).

FIG. 12; Survival curves of animals injected with LPS and treated with the compound ST 722 (1.25 mg/kg/day i.p. from day −7 to day 0).

EXPERIMENTAL MODEL OF ENDOTOXIC SHOCK: EVALUATION OF THE EFFECT OF ST 722 ON LPS-INDUCED SERUM TNF LEVELS IN MICE

Male C57BL/6 inbred mice aged 7 weeks have been utilized (7–15 animals per experimental group). The compound ST 722, solubilized in sterile saline, was administered according to 2 different treatment schedules with respect to LPS injection (30 mg/kg, 0 time), as follows:

a) at −60 min at the dose of 5 mg/kg i.p.

b) first at −60 min and then at +10 min, at the dose of 1.25 or 2.5 mg/kg i.p.

Experimental procedure and Statistical analysis

See the relevant paragraphs in the previous report.

RESULTS

The decrease of LPS-induced serum TNF levels obtained following the different treatments with the compound ST 722 (Table 9) results to be very significant. Moreover, these results are markedly better than those obtained with ST 200, even when the latter was used at a much higher dose.

TABLE 9

Effect of the substance ST 722 on LPS-induced (30 mg/kg, i.p.) serum TNF levels.

| | | | TNF | | |
|---|---|---|---|---|---|
| Substance | Dose (mg/kg) | No. of mice | U/ml (mean ± S.E.) | Variation[a] (%) | P[b] |
| Exp. 1 | | | | | |
| LPS | 30 | 12 | 689.7 ± 98.7 | | |
| ST 722 | 5[a] | 15 | 100.6 ± 17.7 | −85 | <0.001 |
| Exp. 2 | | | | | |
| LPS | 30 | 7 | 196.7 ± 58.7 | | |
| ST 722 | 1.25[b] | 8 | 30.1 ± 6.4 | −85 | <0.01 |
| ST 722 | 2.5[b] | 8 | 26.5 ± 4.5 | −87 | <0.01 |

[a]= The substance ST 722 was administered by i.p. route and at the reported dose at −60 min with respect to LPS challenge.
[b]= The substance ST 722 was administered by i.p. route and at the dose shown at −60 min and +10 min with respect to LPS challenge.
[c]= Percent mean variation of serum TNF levels of ST 722-treated vs. LPS-injected animals.
[d]= Student "t" test.

EXPERIMENTAL MODEL OF ENDOTOXIC SHOCK: EVALUATION OF THE EFFECT OF ST 1037 ON LPS-INDUCED SERUM TNF LEVELS IN MICE

Male C57BL/6 inbred mice (Iffa Credo) aged 7 weeks have been utilized (8 animals per experimental group).

The compound ST 1037, solubilized in sterile saline, was administered by i.p. route (5 mg/kg) at −60 min and by i.v. route (1 mg/kg) at +10 min. with respect to the LPS injection (30 mg/kg, i.p.).

Experimental procedure and Statistical analysis

See the relevant paragraphs in the previous report.

RESULTS

By treating the animals with the substance ST 1037 prior to (at −60 min) and after (at +10 min) the LPS challenge, at the doses of 5 mg/kg i.p. and 1 mg/kg i.v. respectively, a significant reduction (p<0.05) of circulating TNF is obtained (Table 10). this result, at variance with that experimentally found with ST 200. allows us to envisage a protective effect of the compound ST 1037 also on the survival of the mice during endotoxic shock.

TABLE 10

Effect of the substance ST 1037 on LPS-induced (30 mg/kg, i.p.) serum TNF levels.

| Substance | Dose (mg/kg) | No. of mice | TNF U/ml (mean ± S.E.) | Variation[a] (%) | P[b] |
|---|---|---|---|---|---|
| LPS | 30 | 8 | 140.5 ± 24.7 | | |
| ST 1037 | 5 i.p. + 1 i.v. | 8 | 78.3 ± 7.1 | −44 | ≦0.05 |

The compound ST 1037 was administered at the dose of 5 mg/kg i.p. at −60 min and at the dose of 1 mg/kg i.v. at +10 min with respect to the LPS challenge (0 time).
[a]= Percent mean variation of serum TNF of ST 1037-treated vs. LPS-injected animals.
[b]= Student "t" test.

EXPERIMENTAL MODEL OF ENDOTOXIC SHOCK: EVALUATION OF THE PROTECTIVE EFFECT OF ST 1000 ON LPS-INDUCED LETHALITY IN MICE

Male C57BL/6 inbred mice (Iffa Credo) aged 7 weeks have been utilized (8 animals per experimental group).

The compound ST 1000, solubilized in sterile saline, was administered by i.p. route at the dose of 5 mg/kg/day from day −3 through day +4, with respect to the LPS injection (35 mg/kg, i.p.). The protective effect was evaluated in terms of both percent survival and MST as well as health state, as judged by rectal temperature measurements (see Appendix 1).

Experimental procedure and Statistical analysis

See the relevant paragraphs in the previous report.

RESULTS

Treatment with ST 1000 (5 mg/kg/day i.p. from day −3 to day +4) results in some protection (37.5% survival) of the animals intoxicated with LPS (100% lethality), and in a clear prolongation of the MST (4 days vs. 1 day; (p<0.001) (Table 11, FIG. 13).

Figure 14:
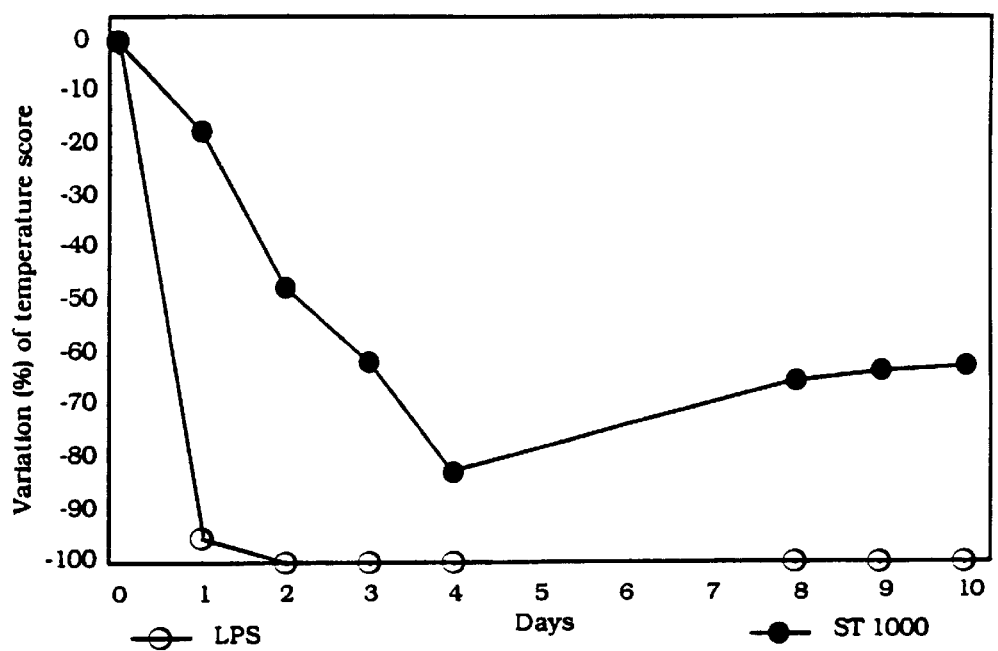

Additionally, the health state of the animals, evaluated by rectal temperature measurements (see experimental conclusion and discussion in Appendix) appears to be markedly ameliorated following treatment with the substance under examination (FIG. 14).

From the whole body of the experimental results, it comes out that the substance ST 1000, as a prospective agent in the therapy of endotoxic shock, has a much better profile than that previously found with ST 200 in this experimental model.

TABLE 11

Protective effect of the substance ST 1000 in a murine model of endotoxic shock. Evaluation of survival and MST.

| Substance | Dose (mg/kg) | Survival S/T (%)[a] | P[b] | (days) | P[d] |
|---|---|---|---|---|---|
| Control | — | 8/8 (100) | | | |
| LPS | 35 | 0/8 (0) | | 1.0 (1.0–1.0) | |
| ST 1000 | 5 | 3/8 (37.5) | n.s. | 4.0 (2.25–≧10.0) | <0.001 |

Treatment was performed by administering the substance ST 1000 by i.p. route at the dose of 5 mg/kg/day from day −3 to day +4, with respect to the day of LPS-challenge (35 mg/kg. i.p.).
[a]= Survivors/Total.
[a]= Fisher exact test.
[b]= Mean Survival Time with range of variation shown in brackets.
[c]= Mann-Whitney "U" test.

Figure 13:
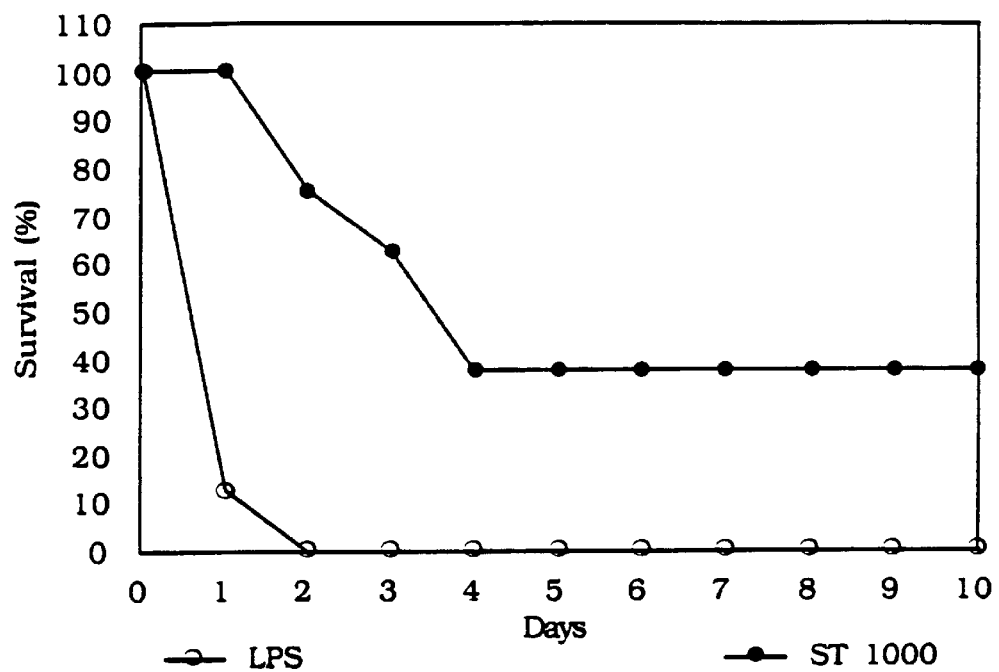

FIG. 13; Survival curves of LPS-injected animals treated with 5 mg/kg/day ST 1000 from day −3 to day +4, with respect to LPS challenge (day 0).

FIG. 14; Health state of the animals evaluated by rectal temperature measurements.

What is claimed is:

1. A pharmacologically acceptable salt of isovaleryl L-carnitine 11-hydroxyundecyl ester.

2. A pharmacologically acceptable salt of isovaleryl L-carnitine 10-hydroxydecyl ester.

3. A pharmaceutical composition, comprising an amount of an ester of claim 1 effective for the treatment of endotoxic shock, and a pharmacologically acceptable excipient.

4. A pharmaceutical composition, comprising an amount of an ester of claim 2 effective for the treatment of endotoxic shock, and a pharmacologically acceptable excipient.

5. A method of treating endotoxic shock comprising administering an effective amount of the pharmacologically acceptable salt of claim 1 to a patient in need thereof.

6. A method of treating endotoxic shock comprising administering an effective amount of the pharmacologically acceptable salt of claim 2 to a patient in need thereof.

7. A method of treating endotoxic shock, comprising administering an effective amount of the pharmaceutical composition of claim 3 to a patient in need thereof.

8. A method of treating endotoxic shock, comprising administering an effective amount of the pharmaceutical composition of claim 4 to a patient in need thereof.

* * * * *